United States Patent
Abe et al.

(10) Patent No.: US 10,547,789 B2
(45) Date of Patent: Jan. 28, 2020

(54) SUBJECT INFORMATION OBTAINING APPARATUS, DISPLAY METHOD, PROGRAM, AND PROCESSING APPARATUS

(71) Applicant: CANON KABUSHIKI KAISHA, Tokyo (JP)

(72) Inventors: Hiroshi Abe, Kyoto (JP); Ayumi Kabata, Kawasaki (JP); Masae Torii, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 410 days.

(21) Appl. No.: 14/758,119

(22) PCT Filed: Dec. 20, 2013

(86) PCT No.: PCT/JP2013/007507
§ 371 (c)(1),
(2) Date: Jun. 26, 2015

(87) PCT Pub. No.: WO2014/103270
PCT Pub. Date: Jul. 3, 2014

(65) Prior Publication Data
US 2015/0334308 A1    Nov. 19, 2015

(30) Foreign Application Priority Data

Dec. 28, 2012  (JP) ................................ 2012-286683
Nov. 20, 2013  (JP) ................................ 2013-240119

(51) Int. Cl.
*H04N 9/47*    (2006.01)
*H04N 5/232*   (2006.01)
(Continued)

(52) U.S. Cl.
CPC ....... *H04N 5/23293* (2013.01); *G02B 21/368* (2013.01); *G06K 9/46* (2013.01);
(Continued)

(58) Field of Classification Search
CPC ............. A61B 5/0095; A61B 5/02007; A61B 5/14532; A61B 5/14542; A61B 5/14552
(Continued)

(56) References Cited

U.S. PATENT DOCUMENTS

2005/0101863 A1 *  5/2005  Kawagishi ............. A61B 8/481
                                                     600/443
2008/0100612 A1    5/2008  Dastmalchi
(Continued)

FOREIGN PATENT DOCUMENTS

EP    1493380 A1    1/2005
JP    H07-75638 A   3/1995
(Continued)

OTHER PUBLICATIONS

Yao et al. ("Label-free oxygen-metabolic photoacoustic microscopy in vivo" by St. Louis, published on Jul. 2011).*

*Primary Examiner* — Masum Billah
(74) *Attorney, Agent, or Firm* — Canon U.S.A., Inc. IP Division

(57) ABSTRACT

An apparatus in related art has a problem in a presentation method of data to a user or a usability. A subject information obtaining apparatus includes a plurality of transducer elements that receive acoustic waves generated in a subject irradiated with light from a light source and transduce the acoustic waves into a plurality of reception signals, a processing unit configured to obtain a characteristic distribution indicating a distribution of characteristic information respectively corresponding to a plurality of positions in the subject by using the plurality of reception signals, in which the processing unit outputs image information for displaying a distribution image created by using the characteristic distribution and data indicating a time fluctuation of the
(Continued)

characteristic information in a predetermined region of the distribution image within a same screen of a display unit.

22 Claims, 7 Drawing Sheets

(51) Int. Cl.
| | |
|---|---|
| G06T 11/20 | (2006.01) |
| G06T 1/20 | (2006.01) |
| H04N 5/265 | (2006.01) |
| G06K 9/46 | (2006.01) |
| G06T 7/00 | (2017.01) |
| G02B 21/36 | (2006.01) |

(52) U.S. Cl.
CPC .............. *G06T 1/20* (2013.01); *G06T 7/0012* (2013.01); *G06T 11/206* (2013.01); *H04N 5/265* (2013.01); *G06K 2009/4666* (2013.01)

(58) Field of Classification Search
USPC .......................................................... 348/77
See application file for complete search history.

(56) References Cited

U.S. PATENT DOCUMENTS

| | | | | |
|---|---|---|---|---|
| 2011/0208057 A1* | 8/2011 | Oikawa | ................ | A61B 5/0095 600/443 |
| 2013/0116537 A1* | 5/2013 | Sato | ..................... | A61B 5/0095 600/407 |
| 2013/0123604 A1* | 5/2013 | Oyama | ................ | A61B 5/0095 600/407 |

FOREIGN PATENT DOCUMENTS

| | | | | |
|---|---|---|---|---|
| JP | H08308831 A | | 11/1996 | |
| JP | 2005218684 A | | 8/2005 | |
| JP | 2010057730 A | | 3/2010 | |
| JP | 2012-217554 A | | 11/2012 | |
| JP | 2012213609 A | * | 11/2012 | ........... A61B 5/0037 |
| JP | 2012217554 A | * | 11/2012 | ........... A61B 5/0095 |
| WO | 2005-122907 A1 | | 12/2005 | |
| WO | 2010-030817 A1 | | 3/2010 | |
| WO | 2012-086842 A1 | | 6/2012 | |
| WO | 2012-103274 A1 | | 8/2012 | |
| WO | 2012-158720 A1 | | 11/2012 | |

* cited by examiner

[Fig. 1A]
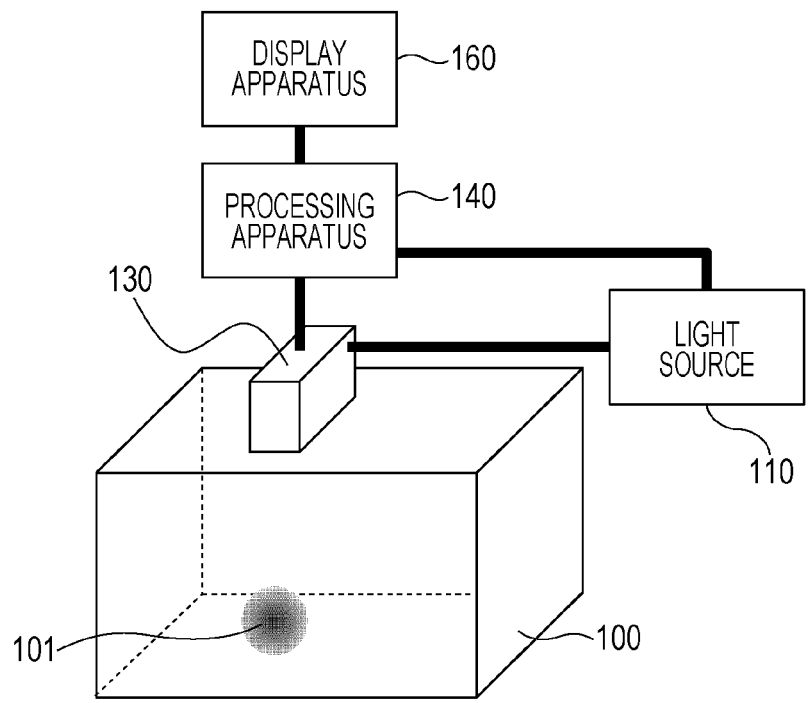
[Fig. 1B]
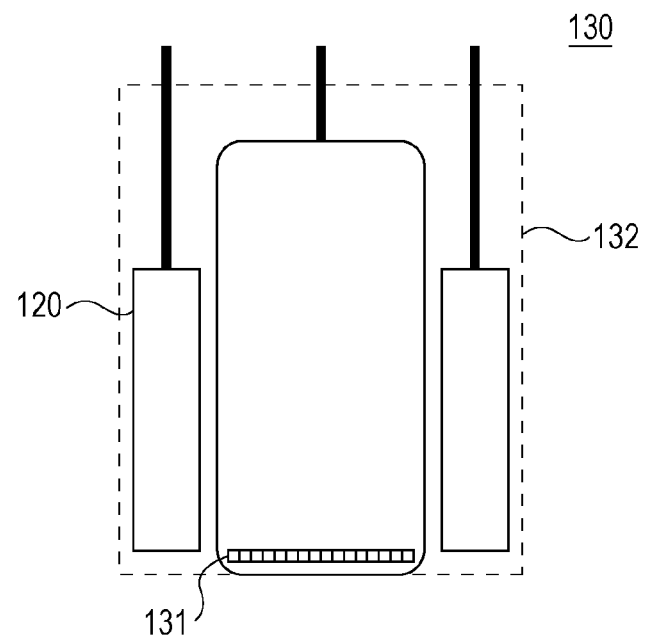

[Fig. 2A]
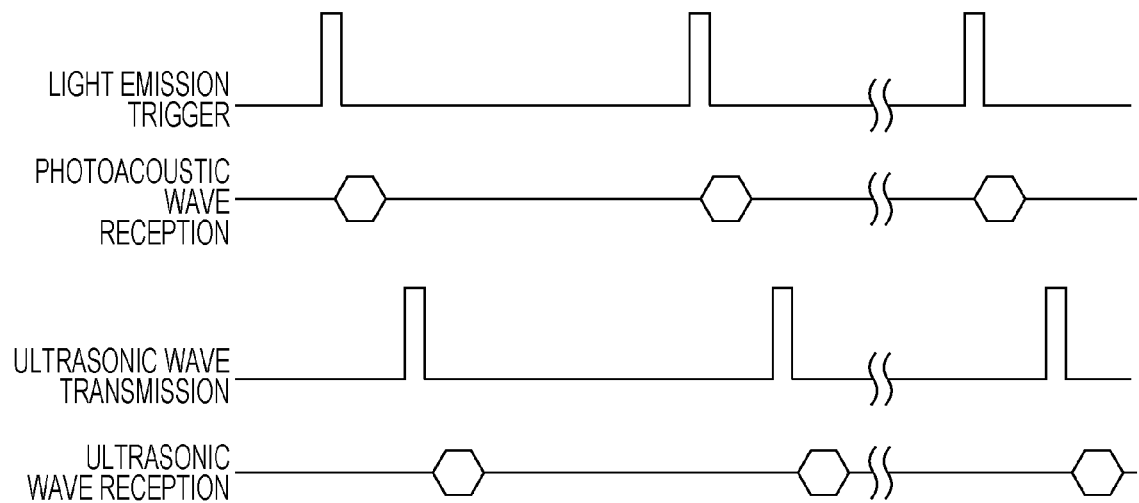
[Fig. 2B]
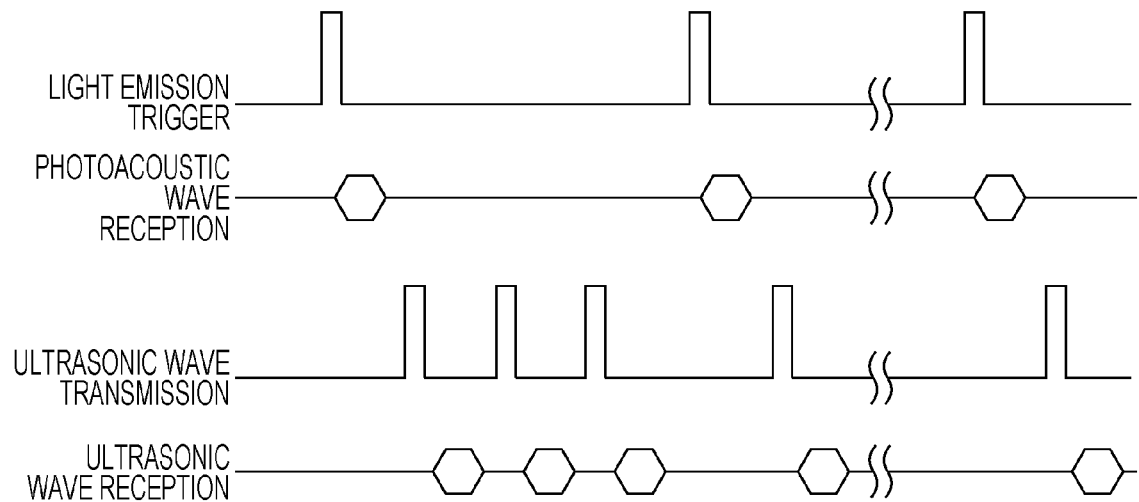

[Fig. 3A]
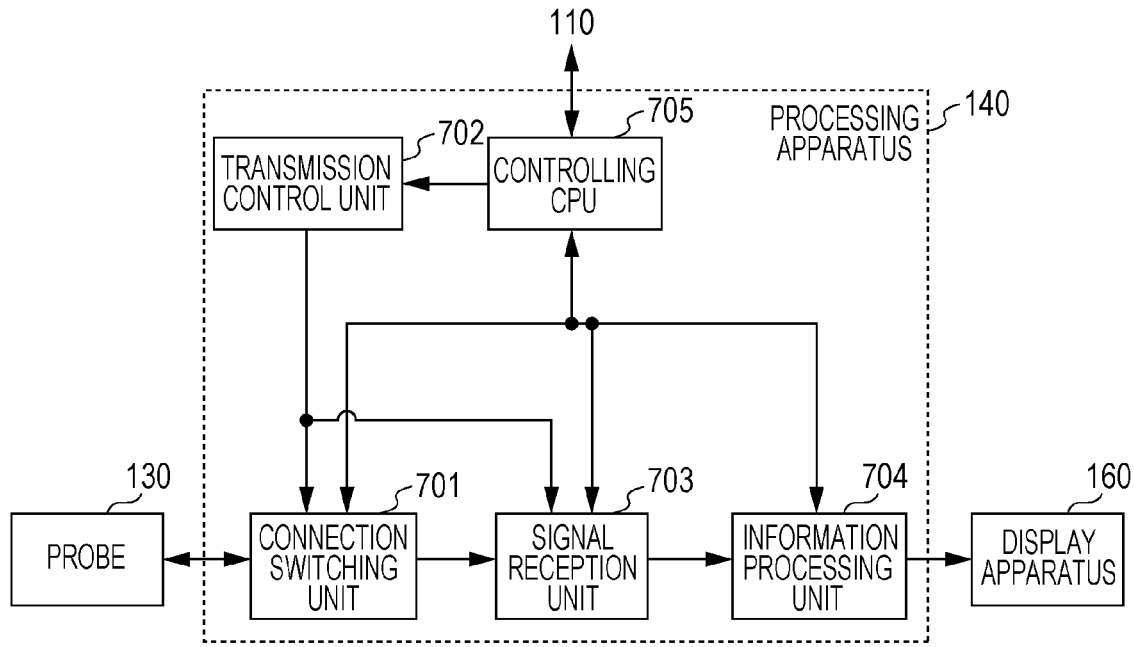
[Fig. 3B]
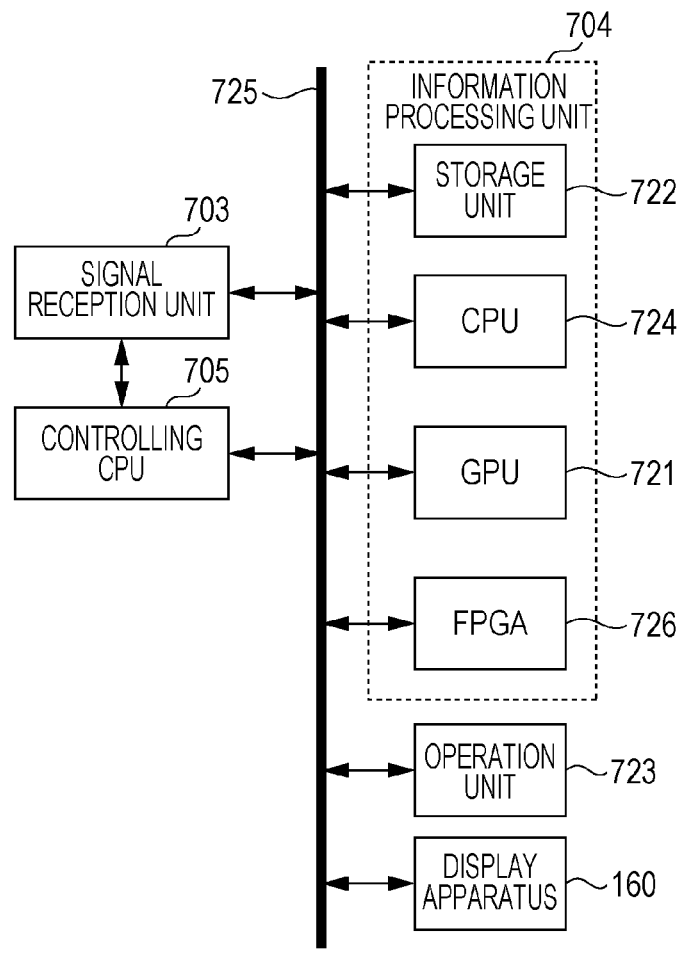

[Fig. 4]
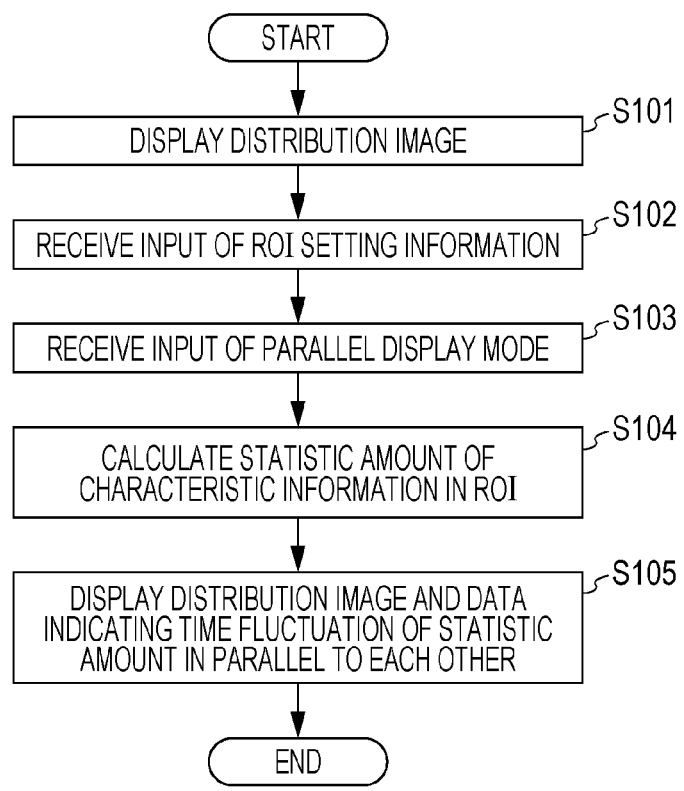

[Fig. 5]
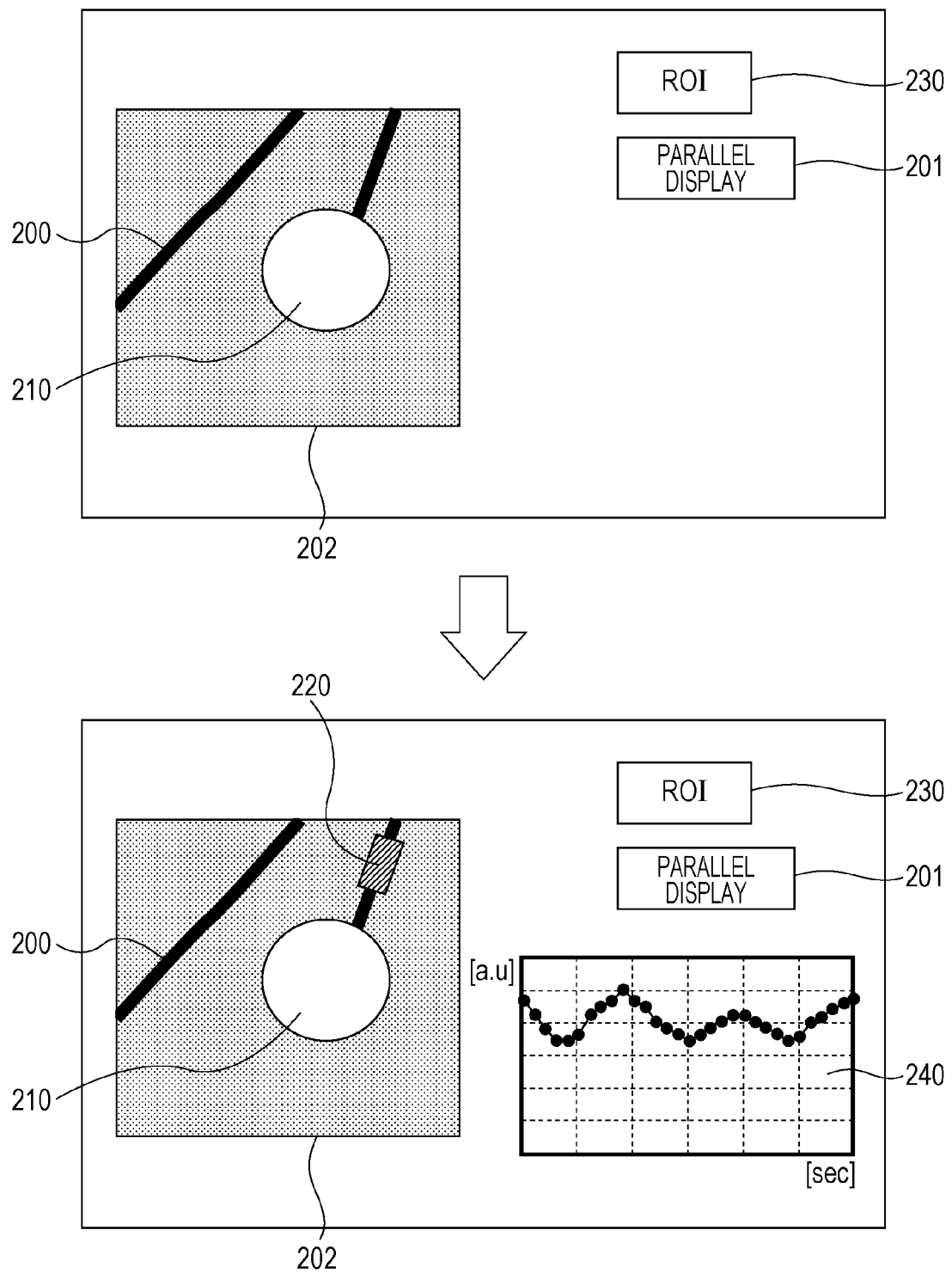

[Fig. 6]
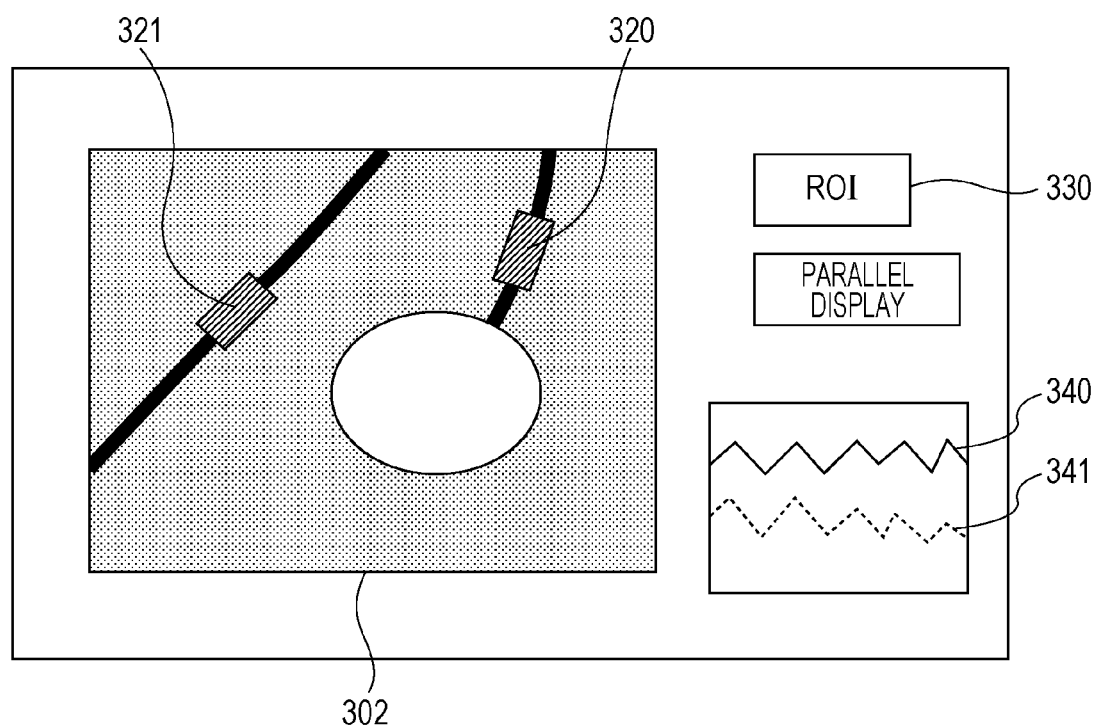

[Fig. 7]
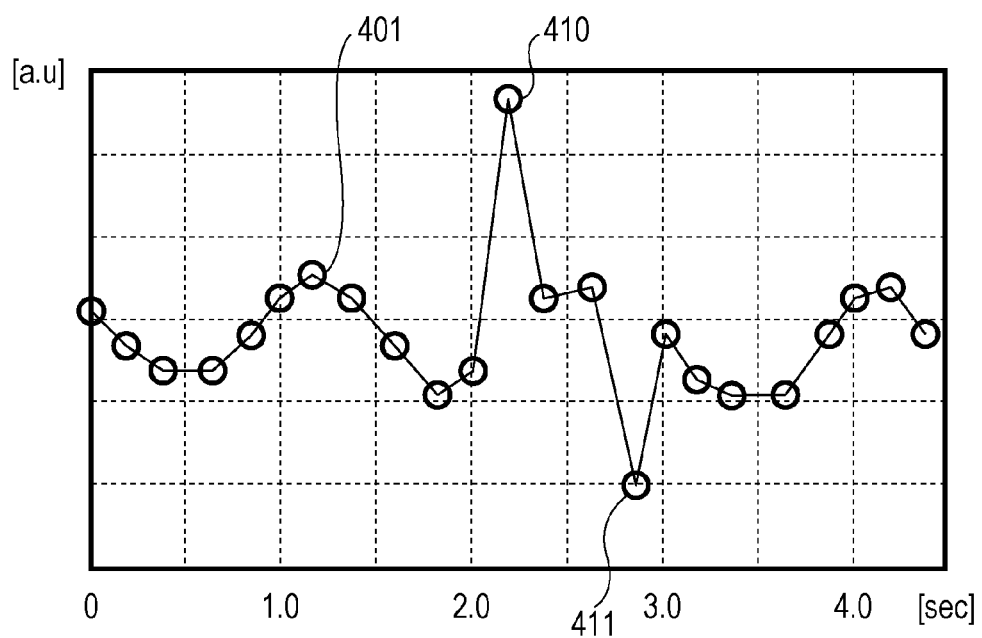

SUBJECT INFORMATION OBTAINING APPARATUS, DISPLAY METHOD, PROGRAM, AND PROCESSING APPARATUS

TECHNICAL FIELD

The present invention relates to a subject information obtaining apparatus, a display method, a program, and a processing apparatus. The invention particularly relates to a technology for obtaining characteristic information by receiving an acoustic wave generated by light.

BACKGROUND ART

Photoacoustic imaging is proposed as one of photo imaging technologies for irradiating a subject with light from a light source and imaging characteristic information in the subject which is obtained on the basis of the incident light. According to the photoacoustic imaging, the subject is irradiated with pulsed light generated from the light source, and an acoustic wave (typically, an ultrasonic wave) generated from a site where energy of the pulsed light propagated and diffused in the subject is absorbed is received. The characteristic information in the subject is then imaged by using the reception signal.

That is, according to the photoacoustic imaging, it is possible to obtain a distribution of the characteristic information (characteristic distribution) related to the light absorption at individual positions in the subject by utilizing a difference of absorption coefficients of light energy between a subject site such as a tumor and the other sites. The obtained characteristic distribution includes an initial sound pressure distribution, a light absorption coefficient distribution, a material concentration distribution, or the like.

According to NPL 1, a blood vessel is imaged by obtaining a total hemoglobin concentration distribution in the subject by a photoacoustic microscopy. With the photoacoustic microscopy according to NPL 1, light is sequentially focused on one point to another point (for each position) on a subject surface, and an acoustic wave generated from each position is sequentially obtained. The characteristic information based on the acoustic wave from the individual position is then arranged one by one. According to NPL 1, oxygen metabolism data such as a time course of oxygen saturation in blood obtained by using the photoacoustic microscopy is indicated, and a recognition that the above-described oxygen metabolism is useful as an index for a diagnosis is described.

CITATION LIST

Non Patent Literature

NPL 1: Label-free oxygen-metabolic photoacoustic microscopy in vivo, Journal Of Biomedical Optics 16(7) 076003 (2011)

SUMMARY OF INVENTION

Technical Problem

In a diagnosis for a tumor or the like, as described in NPL 1, a time fluctuation of the characteristic information may be useful as the index for the diagnosis. However, in case of the photoacoustic microscopy of NPL 1, how the time fluctuation of the characteristic information is presented to an operator (user) is not described. In case of the above-described apparatus used in the diagnosis, it is important to improve the method of presentation the data to the user and a usability.

The photoacoustic microscopy according to NPL 1 adopts a system in which the light is focused on one point to another point on the subject surface for the sequential scanning, and the obtained characteristic information is arranged one by one. As a system different from the above-described system, a system is proposed in which plural positions are irradiated with the light at once, and plural reception signals based on acoustic waves generated from the plural positions are used for the image reconstruction. According to the system of the photoacoustic microscopy described in NPL 1, a higher resolution is advantageous as compared with the system for carrying out the above-described image reconstruction, but it takes time. Particularly, in a case where a subject in a relatively wide range such as breasts is inspected, it takes long time, and a problem of the usability occurs.

In view of the above, the present invention provides a subject information obtaining apparatus with a satisfactory usability which can perform a presentation useful to a diagnosis, a display method, a program, and a processing apparatus.

Solution to Problem

According to an aspect of the present invention, there is provided a subject information obtaining apparatus including a light source that generates light, a plurality of transducer elements configured to receive acoustic waves generated in a subject that is irradiated with the light from the light source and transduce the acoustic waves into a plurality of reception signals, and a processing unit configured to obtain a characteristic distribution indicating a distribution of characteristic information respectively corresponding to a plurality of positions in the subject by using the plurality of reception signals, in which the processing unit outputs image information for displaying a distribution image created by using the characteristic distribution and data indicating a time fluctuation of the characteristic information in a predetermined region of the distribution image within a same screen of a display unit.

According to another aspect of the present invention, there is provided a display method of displaying an image on a display unit by using a characteristic distribution obtained in a subject information obtaining apparatus by receiving acoustic waves generated in a subject that is irradiated with light, the obtained characteristic distribution being a distribution of characteristic information respectively corresponding to a plurality of positions in the subject obtained by using a plurality of reception signals that are obtained by receiving the acoustic waves, the display method including displaying a distribution image created by using the characteristic distribution and data indicating a time fluctuation of the characteristic information in a predetermined region of the distribution image within a same screen of the display unit.

Further features of the present invention will become apparent from the following description of exemplary embodiments with reference to the attached drawings.

BRIEF DESCRIPTION OF DRAWINGS

FIG. 1A is a schematic diagram of a subject information obtaining apparatus according to a first embodiment.

FIG. 1B is a schematic diagram of the subject information obtaining apparatus according to the first embodiment.

FIG. 2A is a timing chart of a reception timing of an acoustic wave according to the first embodiment.

FIG. 2B is a timing chart of the reception timing of the acoustic wave according to the first embodiment.

FIG. 3A is a schematic diagram of a processing apparatus according to the first embodiment.

FIG. 3B is a schematic diagram of the processing apparatus according to the first embodiment.

FIG. 4 is a flow chart of a flow for a display method according to the first embodiment.

FIG. 5 is a schematic diagram of an example of a screen displayed on a display unit according to the first embodiment.

FIG. 6 is a schematic diagram of an example of the screen displayed on the display unit according to the first embodiment.

FIG. 7 is a schematic diagram of an example of the screen displayed on the display unit according to a second embodiment.

DESCRIPTION OF EMBODIMENTS

Hereinafter, embodiments of the present invention will be described by using the drawings. The same components are principally assigned with the same reference signs, and a description thereof will be omitted.

In the following description, an acoustic wave includes an elastic wave called photoacoustic wave, optical ultrasound wave, sound wave, or ultrasonic wave, and an acoustic wave generated through light irradiation is called "photoacoustic wave", in particular. A subject information obtaining apparatus according to the following embodiments receives at least photoacoustic waves generated at plural positions (sites) in a subject by irradiating the subject with light (an electromagnetic wave including visible light or infra-red ray) and obtains a characteristic distribution indicating a distribution of characteristic information respectively corresponding to the plural positions in the subject.

The characteristic information obtained on the basis of the photoacoustic wave indicates characteristic information related to a light absorption and includes an initial sound pressure of the photoacoustic wave generated through the light irradiation or characteristic information on which a light energy absorption density, an absorption coefficient, a material concentration constituting tissues, or the like which is derived from the initial sound pressure is reflected. The material concentration includes, for example, an oxygen saturation, a total hemoglobin concentration, an oxyhemoglobin or deoxyhemoglobin concentration, or the like.

Among the acoustic waves, an acoustic wave transmitted from a probe may be called "ultrasonic wave", and a wave where the transmitted ultrasonic wave is reflected in the subject may particularly be called "reflection wave" in some cases. In this manner, the subject information obtaining apparatus according to the following embodiments may obtain a distribution related to an acoustic characteristic in the subject not only by receiving the photoacoustic wave but also by receiving the reflection wave based on an ultrasonic echo. The distribution related to this acoustic characteristic includes a distribution on which a difference in acoustic impedances of tissues in the subject is reflected. However, according to the embodiments of the present invention, it suffices even if the ultrasonic wave is not transmitted or received or the distribution related to the acoustic characteristic is not obtained.

Furthermore, the subject information obtaining apparatus according to the following embodiments is mainly aimed at a diagnosis on a malignant tumor of a person or an animal, a blood vessel disease, or the like, a progress observation of a chemical treatment, or the like. Therefore, a living body is supposed as a subject, and specifically, a diagnosis target such as breasts, a cervical part, or an abdominal part of a person or an animal is supposed.

Tissues having a relatively high absorption coefficient in the subject indicate a light absorber in the subject. For example, when a part of a human body is a subject, the light absorber includes a blood vessel include a large amount of oxyhemoglobin or deoxyhemoglobin or a large amount of those, a tumor including a large number of new blood vessels, a plaque of the carotid wall, or the like. Moreover, a molecular probe specifically-bound to a malignant tumor or the like by utilizing gold particles, graphite, or the like, a capsule that conveys a medical agent, or the like also is the light absorber.

First Embodiment

Hereinafter, a first embodiment will be described by using the drawings. First, a configuration of the subject information obtaining apparatus will be described, and a display method will be described thereafter.

Overall Configuration

First, an overall configuration of the subject information obtaining apparatus according to the present embodiment will be described by using FIGS. 1A and 1B. FIG. 1A is a schematic diagram of the subject information obtaining apparatus according to the present embodiment, and FIG. 1B is a schematic diagram of a probe 130. The subject information obtaining apparatus according to the present embodiment at least includes a light source 110, the probe 130 provided with plural transducer elements 131, and a processing apparatus 140 that functions as a processing unit. The probe 130 according to the present embodiment is configured to perform both the reception of the photoacoustic wave and the transmission and reception of the photoacoustic wave. The processing apparatus 140 can obtain both the characteristic distribution based on the photoacoustic waves and the distribution related to the acoustic characteristic based on the reflection waves by the ultrasonic wave echo.

In FIG. 1A, the light generated by the light source 110 is guided into the probe 130 via an optical member such as bundle fiber, and the light is emitted from an outgoing terminal 120 in the probe 130 to a subject 100. The light emitted to the subject 100 is diffused in the subject and absorbed by a light absorber 101 in the subject, so that the photoacoustic wave is generated. The plural transducer elements 131 provided to the probe 130 receive the photoacoustic waves generated from the subject 100 and respectively transduce the photoacoustic waves into electric signal (reception signals). The plural reception signals output from the probe 130 are sent to the processing apparatus 140.

The apparatus according to the present embodiment includes a configuration in which the light for the one irradiation reaches plural positions in the subject instead of focusing the light on a single position (one point) on a subject surface like a photoacoustic microscopy. The probe 130 includes the plural transducer elements 131. Therefore, it is possible to receive the photoacoustic waves generated from the plural positions in the subject at least by one light irradiation. To elaborate, it is possible to obtain a characteristic information group in a predetermined region composed of plural positions (plural points). The characteristic information group is equivalent to a characteristic distribution indicating a distribution of the characteristic information for each position.

The plural transducer elements 131 also transmit the ultrasonic waves to the subject 100 while a timing is shifted from the timing for the reception of the photoacoustic waves described above. The transmitted ultrasonic waves are reflected in the subject, and the plural transducer elements 131 receive the returned reflection waves and respectively transduce the reflection waves into analog electric signals (reception signals). The plural reception signals output from the plural transducer elements 131 are sent to the processing apparatus 140.

Here, controls on the respective timing for the light emission from the light source 110, the reception of the photoacoustic wave, the transmission of the ultrasonic wave, and the reception of the reflection wave will be described.

Timings for Light Emission and Transmission and Reception

FIGS. 2A and 2B are timing charts indicating the respective timings. In FIGS. 2A and 2B, a light emission trigger indicates a light irradiation timing. A detection signal from a light sensor such as a photo diode that detects the light from the light source 110 or a light emission instruction signal from the processing apparatus 140 can be used as the light emission trigger. Since the propagation speed of the light is sufficiently higher than the propagation speed of the acoustic wave, the light emission timing by the light source and the timing at which the subject is irradiated with the light can be dealt with as the same time.

In FIG. 2A, after the light emission from the light source, the processing apparatus 140 causes a transmission and reception unit 6 to receive the photoacoustic wave. A time between the light emission and the start of the reception of the photoacoustic wave is preferably as short as possible. Next, after the reception of the photoacoustic wave, the processing apparatus 140 sends a transmission signal for transmitting the ultrasonic wave from the transducer elements 131 to the transducer elements 131. The transmission and reception of the ultrasonic wave in FIG. 2A is conducted once between the light emission and the next light emission, but the configuration is not limited to this. The ultrasonic wave may be transmitted and received by plural times between the light emission and the next light emission as illustrated in FIG. 2B. In FIG. 2B, the transmission and reception of the ultrasonic wave is conducted by three times, but the number of transmission and reception is also arbitrary.

Furthermore, the transmission and reception of the ultrasonic wave may not be conducted between the light emission and the next light emission. After the light emission and the reception of the photoacoustic wave are repeatedly conducted by a predetermined number of times, the transmission and reception of the ultrasonic wave may be conducted after the last light emission and the last photoacoustic wave reception (in the predetermined number-th time). Alternatively, after the transmission and reception of the ultrasonic wave is repeatedly conducted by a predetermined number of times, the light emission and the reception of the photoacoustic wave may be conducted after the last transmission and reception of the ultrasonic wave (in the predetermined number-th time).

Next, respective configurations of the subject information obtaining apparatus according to the present embodiment will be described in detail.

Light Source 110

A pulsed light source that can generate pulsed light at an order of nano seconds to micro seconds is preferably used for the light source 110. Specifically, to efficiently generate the photoacoustic waves, a pulse width having approximately 10 nano seconds is used. In addition, a wavelength between 500 nm and 1200 nm is preferably used. For a specific light source, a pulsed laser such as an Nd:YAG laser or an alexandrite laser is preferably used. A Ti:sa laser or an OPO laser using Nd:YAG laser light as excitation light may also be used. In addition to the above, a solid laser, a gas laser, a dye laser, a semiconductor laser, and the like can also be used. An optical member such as bundle fiber, a mirror, prism, or the like may be used for the light transmission from the light source 110 to the probe 130.

Probe 130

As illustrated in FIG. 1B, the probe 130 includes a transducer provided with the plural transducer elements 131 and the outgoing terminal 120 that functions as an irradiation unit. The probe 130 is preferably covered with a housing 132. The outgoing terminal 120 is composed of fiber, a lens, a diffused plate, or the like and irradiates the subject with light having a desired shape. The plural transducer elements 131 receive the photoacoustic waves and respectively transduce the photoacoustic waves into reception signals (first reception signals).

The transducer elements 131 according to the present embodiment can transmit the ultrasonic wave to the subject on the basis of a transmission signal from the processing apparatus 140. The transmitted ultrasonic waves are reflected on the basis of a difference in the acoustic impedances in the subject. The plural transducer elements 131 receive reflection waves returning from the subject and respectively transduce the reflection waves into reception signals (second reception signals).

Any transducer elements such as piezoelectric elements using piezoelectric phenomena, the transducer elements using light resonances, and the transducer elements using changes in capacitances such as CMUT may be used for the transducer elements 131 so long as the elements can receive the acoustic waves and transduce the acoustic waves into the electric signals. According to the present embodiment, the common transducer elements 131 double as the transducer elements that receive the photoacoustic waves and the transducer elements that transmit the ultrasonic waves and receive the reflection waves. However, for the probe according to the embodiments of the present invention, a transducer provided with plural transducer elements that receive the photoacoustic waves and a transducer provided with plural transducer elements that transmit and receive the ultrasonic waves may separately be structured. In addition, not only a type in which the user operates the probe while grabbing the probe by hand but also a type in which the probe 130 is mechanically moved may be used for the probe 130 according to the present embodiment.

The plural transducer elements 131 may be arranged in a plane called 1D array, 1.5D array, 1.75D array, or 2D array. The plural transducer elements 131 may also be arranged in an arc shape.

Furthermore, the plural transducer elements 131 may also be arranged in a supporting body having a bowl shape. Specifically, as described in International Publication No. 2010/030817, reception surfaces of the plural transducer elements 131 may be arranged in a three-dimensional spiral on a bowl-shaped inner surface of the supporting body. The above-described arrangement is preferably adopted since the photoacoustic waves can be received at a wide angle. In above-described arrangement, respective directional axes (axes along a direction in which a reception sensitivity is highest) of at lease a part of transducer elements among the plural transducer elements 131 gather in a particular area.

With the above-described arrangement, it is possible to receive the photoacoustic waves generated from the particular area at an even higher sensitivity. A distribution image having a high resolution where a connection between diagnosis targets such as blood vessels is satisfactory can be obtained by using the reception signals obtained from the transducer elements 131 arranged in the above-described arrangement.

An acoustic medium in a state of liquid, gel, or the like (for example, water may also be used) having an acoustic impedance close to the subject is preferably provided between reception surfaces of the plural transducer elements 131 arranged on an inner side of the bowl and the subject.

Processing Apparatus 140

The processing apparatus 140 performs an amplification of the reception signal derived from the photoacoustic wave which is output from the probe 130 (the reception signal obtained by receiving the photoacoustic wave) or the reception signal derived from the ultrasonic wave (the reception signal obtained by receiving the reflection wave), digital conversion processing, filter processing, and the like. The processing apparatus 140 then uses the respective reception signals on which the signal processing has been conducted and can create photoacoustic image data or ultrasonic image data. Hereinafter, a detailed configuration of the processing apparatus 140 will be described by using FIGS. 3A and 3B.

FIG. 3A is a schematic diagram of a configuration of the processing apparatus 140 according to the present embodiment. The processing apparatus 140 in FIG. 3A includes a connection switching unit 701 that switches a connection state between the probe 130 and the processing apparatus 140, a transmission control unit 702, a signal reception unit 703, an information processing unit 704, and a controlling CPU 705 that functions as a control unit.

The controlling CPU 705 supplies data and control signals used for controlling the respective blocks. Specifically, the controlling CPU 705 controls the light emission instruction signal for instructing the light source 110 to perform the light emission and the transmission signal transmitted by the transmission control unit 702 to the transducer elements 131. The controlling CPU 705 also sends a signal for switching the connection destination of the plural transducer elements 131 to the connection switching unit 701 and supplies the signal reception unit 703 with a control signal and a parameter used for the signal reception control. Furthermore, the controlling CPU 705 supplies the information processing unit 704 with a parameter, a control signal, and the like for causing the information processing unit 704 to determine whether a digital signal transferred from the signal reception unit 703 to the information processing unit 704 is desired from the photoacoustic wave or the ultrasonic wave.

The transmission control unit 702 outputs the transmission signal while following the control of the controlling CPU 705. The signal reception unit 703 converts plural reception signals output from the plural transducer elements 131 into digital signals. The signal reception unit 703 is composed of an A/D conversion unit, a data memory, a multiplexer, and the like. The reception signal derived from the photoacoustic wave and the reception signal derived from the ultrasonic wave may be processed by using the common A/D conversion unit, the common data memory, and the like which are prepared for each channel. The separate A/D conversion units, the separate data memory, and the like may also be prepared for the reception signal derived from the photoacoustic wave and for the reception signal derived from the ultrasonic wave. The digital signals generated in the signal reception unit 703 are transferred to the information processing unit 704.

The connection switching unit 701 switches a connection destination of the plural transducer elements 131. The plural transducer elements 131 are connected to the transmission control unit 702 or connected to the signal reception unit 703 by the connection switching unit 701.

The information processing unit 704 generates the photoacoustic image data and the ultrasonic image data, respectively, from the digital signal derived from the photoacoustic wave and the digital signal derived from the ultrasonic wave transferred from the signal reception unit 703. The information processing unit 704 can conduct appropriate signal processing and image processing in accordance with whether the reception signal is the signal derived from the photoacoustic wave or the signal derived from the reflection wave. Typically, when the ultrasonic image data is generated, delay & sum is conducted where a delay time in accordance with a reaching time of the reflection wave is added to the reception signals from the respective elements to adjust a phase and addition is conducted. When the photoacoustic image data is generated, an image reconstruction to which another algorithm other than the delay & sum is applied may be conducted. For example, an image reconstruction method of generating the photoacoustic image includes a reverse projection method based on a time domain or a Fourier domain which is normally used in a tomography technology or the like. With this configuration, it is possible to obtain the photoacoustic image data or the ultrasonic image data on the basis of the reception signal. The image created by the information processing unit 704 may be a 2D image or 3D image.

The information processing unit 704 can obtain the characteristic distribution indicating the distribution of the characteristic information respectively corresponding to the plural positions in the subject as the photoacoustic image data by at least the single light irradiation. The characteristic information respectively corresponding to the plural positions refers to values corresponding to plural pixels or voxels in the created image, and the respective pixel values or voxel values reflect the initial sound pressure value, the absorption coefficient value, the material concentration value, or the like.

As in FIG. 2B where the light irradiation is repeatedly conducted by plural times, a compound distribution obtained by compounding the plural characteristic distributions obtained by the plural light irradiations to each other can also be generated as the photoacoustic image data. The compound refers to superposition processing conducted among the images such as arithmetic average processing, geometrical mean processing, or harmonic average processing with respect to the plural images or the plural images where a displacement correction is applied to displacements between the respective images.

The information processing unit 704 applies various correction processing such as a luminance correction, a distortion correction or a cutout of an attention region to the created photoacoustic image data and creates a distribution image for the display. Furthermore, the photoacoustic image data and the ultrasonic image data are superposed on each other, and a superposition image illustrated in FIG. 5 can also be created and displayed as the distribution image. The obtained ultrasonic image data includes a distribution related to the acoustic characteristic in the subject.

Furthermore, the plural characteristic distributions obtained in time series by the plural light irradiations may be switched (updated) in time series at a certain time interval and displayed. The certain time interval may be, for example, a same cycle as the light emission (0.1 sec interval in case of the light emission at 10 Hz) or 1 sec interval so that visual observation can be conducted. The update may be conducted each time the compound distribution is obtained not only in the characteristic distribution but also in the above-described compound distribution.

Furthermore, the information processing unit 704 according to the present embodiment can also generate data indicating the time fluctuation of the characteristic information in a predetermined region among the created distribution image. A time fluctuation of the characteristic information may refer to a time fluctuation of the characteristic information at a predetermined position or a time fluctuation of the statistic amount of the characteristic information respectively corresponding to the plural positions in the predetermined region (that is, plural pieces of characteristic information). The statistic amount refers to a statistic result such as an average value, a median value, a mode value, a maximum value, a standard deviation, or a square mean error. To elaborate, the statistic amount of the plural characteristic information in the specified region refers to an average or the like of the plural pixel values or the plural voxel values in the specified region. Any data may be used for the data indicating the time fluctuation of the characteristic information created by the information processing unit 704 so long as the time course is figured out like a line chart illustrated in FIG. 5.

The information processing unit 704 according to the present embodiment can create image information for displaying the distribution image created by using the characteristic distribution and the data indicating the time fluctuation within the same screen and output the image information to a display apparatus 160. Examples of a flow of the display method and the display screen will be described below by using FIGS. 4 and 5, and first, a specific configuration of the information processing unit 704 will first be described.

Specific Configuration of Information Processing Unit 704

FIG. 3B illustrates a configuration of the information processing unit 704 and a vicinity thereof according to the present embodiment. The information processing unit 704 is typically composed of a graphics processing unit (GPU), a work station to which a CPU is mounted, or the like.

A storage unit 722 stores the digital signal transferred from the signal reception unit 703 and setting information related to a measurement operation. The digital signal derived from the photoacoustic wave or the ultrasonic wave which is transferred from the signal reception unit 703 is first stored in the storage unit 722.

A CPU 724 receives instructions related to various operations from a user via an operation unit 723 and generates control information to be used to control the respective functions via a system bus 725. The CPU 724 can perform integration processing or the like on the digital signal derived from the photoacoustic wave which is stored in the storage unit 722. The integration processing refers to processing of repeatedly performing the light irradiation on the same position (scanning position) with respect to the subject and the reception of the photoacoustic wave and integrating the plural obtained reception signals with each other (including an integration average). The system noise is reduced, and the S/N ratio of the reception signal is improved through this integration processing. In a case where an object such as a contrast medium where a generation source of the photoacoustic wave is moved over time is set as a diagnosis target, a movement path over the accumulated time can be figured out. It is noted that similar processing can be conducted by the controlling CPU 705, a GPU 721, or the like.

The CPU 724 writes the digital signal after the integration processing again in the storage unit 722. The digital signal is used for generating the photoacoustic image data by the GPU 721. The CPU 724 also receives the information on the specified region that has been specified by the user and can calculate the statistic amount of the characteristic information respectively corresponding to the plural positions in the specified region.

An FPGA 726 uses the digital signal derived from the ultrasonic wave which is written in the storage unit 722 to perform the delay & sum and creates the ultrasonic image data. The FPGA 726 is composed of a field programmable gate array (FPGA) chip.

The GPU 721 uses the digital signal on which the integration processing is conducted and which is written in the storage unit 722 by the CPU 724 to create the photoacoustic image data. The GPU 721 can also apply various correction processing such as a luminance correction, a distortion correction or a cutout of an attention region to the created photoacoustic image data or the created ultrasonic image data and create the distribution image. Furthermore, the GPU 721 can perform processing of creating the superposition image obtained by superposing the photoacoustic image data and the ultrasonic image data as the distribution image on each other and generate the image information for displaying the data indicating the time fluctuation of the characteristic information and the distribution image in parallel. Similar processing can also be conducted by the CPU 724 or the like. In addition, according to the present embodiment, the photoacoustic image data is created by the GPU 721, and the ultrasonic image data is created by the FPGA 726. However, it is also possible to create the photoacoustic image data and the ultrasonic image data by the common GPU, FPGA, CPU, or the like.

Operation Unit 723

The operation unit 723 is an input apparatus for the user to perform specification of parameters related to the obtaining operation for the characteristic information and various inputs. An input of a parallel display which will be described below and a setting on a region of interest (ROI) as a specified region are also conducted by the operation unit 723. It is noted that when a 3D image is displayed as the distribution image, the ROI can also be specified by way of 3D. A size and a coordinate system of the ROI can arbitrarily changed, and a range of the ROI can be confirmed and specified by the user since the range of the ROI is overlapped and displayed on the distribution image. The operation unit 723 is generally composed of a mouse, a key board, a touch panel, or the like. The operation unit 723 may be separately prepared and connected to the subject information obtaining apparatus instead of the configuration where the subject information processing apparatus includes the operation unit 723.

Display Apparatus 160

The display apparatus 160 that functions as a display unit is composed of a liquid crystal display (LCD), a cathode ray tube (CRT), an organic EL display, or the like. The display apparatus 160 may be separately prepared and connected to the subject information obtaining apparatus instead of the configuration where the subject information processing apparatus includes the display apparatus 160.

Next, examples of a display method and a display screen according to the present embodiment will be described.

Display Method and Display Screen

A display flow according to the present embodiment will be described by using FIG. 4 and FIG. 5. FIG. 4 is a flow chart illustrating the display flow according to the present embodiment, and FIG. 5 is a schematic diagram of an example of a display screen according to the present embodiment.

The display flow according to the present embodiment will be described while a state in which the compound distribution as the photoacoustic image data and the ultrasonic image data are created is set as start. Specifically, in a case where the subject is irradiated with the light by a plural number of times (for example, the irradiation by a predetermined number of times: approximately 30 times), the processing apparatus 140 receives plural reception signals output from the plural transducer elements for a predetermined number of times for each light emission timing (for example, for each light emission timing at a frequency of 10 Hz). The processing apparatus 140 then creates the characteristic distribution for the predetermined number of times to be averaged arithmetically to create the compound distribution.

In S101 of FIG. 4, the processing apparatus 140 superposes the compound distribution and the ultrasonic wave image on each other and displays the resultant image as the superposition image on the display apparatus 160 as the distribution image. An upper drawing of FIG. 5 illustrates the display screen at that time. Since a distribution image 202 of FIG. 5 is a superposition image, a difference in the acoustic impedance in the subject is represented by the ultrasonic wave image, and shape information such as a cancer boundary is represented. Function information including the concentration of the particular materials such as hemoglobin or the like is represented by the photoacoustic wave image. When the superposition image is displayed, the ultrasonic wave image is displayed in gray scale, and the photoacoustic image is displayed in color scale. In addition, a transparency is set, so that it becomes easier to visually recognize each of the images. With the above-described superposition display, it is possible to display a region 210 regarded as a cancer affected area corresponding to a region where the difference in the acoustic impedance is large and a region 200 regarded as a blood vessel corresponding to a region where the light absorption is large.

Next, when an ROI setting icon 230 on the screen is clicked by the user by using a mouse that serves as the operation unit 723 in a state where the distribution image 202 is displayed, a rectangular ROI 220 is displayed on the distribution image. When the rectangular ROI 220 is moved and confirmed by a mouse operation, in S102, the processing apparatus 140 receives setting information on the ROI as information on the specified region from the user.

Subsequently, when the user clicks a parallel display icon 201, in S103, the processing apparatus 140 receives an input of a parallel display mode.

When the input of the parallel display mode is received, in S104, the processing apparatus 140 calculates an average value of the plural characteristic information in the ROI as the statistic amount of the plural characteristic information in the ROI. To elaborate, an average value of the plural pixel values or the plural voxel values in the ROI is calculated. At this time, this average value is calculated for each of the plural characteristic distributions used for creating the compound distribution.

Next, in S105, the processing apparatus 140 displays, as data 240 indicating the time fluctuation of the calculated statistic amount, the data 240 indicating the time fluctuation for each light irradiation of the calculated average value of the plural characteristic information in parallel next to the distribution image 202 (see a lower drawing of FIG. 5). It is noted that according to the present specification, the "parallel display" includes not only a case where the items are arranged on the right and left in the screen as in FIG. 5 but also a case where the items are arranged on the top and bottom or a case where the items are randomly arranged. It suffices if those items are displayed within the single screen.

According to the present embodiment, in addition to the parallel display, the distribution image 202 and the data 240 indicating the time fluctuation may be superposed on each other. To elaborate, the processing apparatus 140 preferably performs the control to establish a state in which the distribution image 202 and the data 240 indicating the time fluctuation are both displayed at a certain timing. The state in which both the image and the data are displayed is not limited to a case where the distribution image 202 and the data 240 indicating the time fluctuation are displayed at the same time (the display start timings are identical to each other). Even when the distribution image 202 and the data indicating the time fluctuation 204 are started to be displayed at different timings, it suffices if a state is established in which both the image and the data are displayed at a certain timing.

The processing apparatus 140 outputs the image information for displaying the distribution image 202 and the data 240 indicating the time fluctuation within the same screen to the display apparatus 160 as described above. According to this, it is facilitated to compare the distribution image with the data related to the time fluctuation, and the user may also readily grasp which position the time fluctuation corresponds to, so that the usability is improved.

In the lower diagram of FIG. 5, the displayed data 240 indicating the time fluctuation indicates the time fluctuation of the average value of the characteristic information for each light irradiation (to elaborate, the time fluctuation at the same cycle as the light irradiation cycle). For example, in case of the light emission frequency at 10 Hz, changes of the characteristic information by 0.1 sec are displayed. According to this, for example, it is possible to check a temporal transition of an average intensity in the ROI of the characteristic information based on a difference in contractions caused by a pulsing motion of a blood vessel. As a result, it is possible to conduct a confirmation on a local blood deficiency state, a diagnosis on a medicine propagation through a blood vessel to a cancer affected area, and the like, and a diagnosis accuracy may be improved. However, the cycle indicating the time fluctuation is not limited to the time fluctuation for each light irradiation and may be the time fluctuation for every predetermined number of times of the light irradiations. In addition, the time fluctuation at a predetermined cycle (preferably, at a cycle of 1 sec or shorter) irrespective of the light irradiation may be displayed.

According to the present embodiment, steps of S102 and S103 may be reversed. When the ROI setting is received in S102 while the parallel display icon 201 is omitted, the steps of S103 and S104 may automatically be executed. At the time of the ROI setting, a closed curve may be created on the screen by click and drag of the mouse to set a free-form ROI. If the free-form ROI can be set, noise called artifact or a region that is to be intentionally excluded can be avoided.

Therefore, only a region used for the diagnosis can be extracted, so that the usability is improved.

In the example of FIG. 5, the time fluctuation of the characteristic information in the ROI specified by the user is displayed. However, not only the ROI specified by the user but also the time fluctuation of the characteristic information in the region extracted by the processing apparatus 140 on the basis of the distribution image may be displayed. Specifically, it is conceivable that the processing apparatus 140 automatically extracts a region where the value of the characteristic information in the distribution image is higher than a predetermined value as the ROI.

The distribution image is not limited to the superposition image obtained by superposing the compound distribution (compound image with the characteristic distribution that serves as the photoacoustic image) and the distribution related to the acoustic characteristic (the ultrasonic wave image) on each other. The distribution image may be the distribution image composed of only the characteristic distribution or the distribution image composed of the compound distribution.

Furthermore, the distribution images obtained in time series may be switched (updated) in time series at a certain time interval and displayed. The certain time interval is a predetermined time interval such as a cycle at which the distribution image is obtained. For example, the certain time interval may be the same cycle as the light emission (0.1 sec interval in case of the light emission at 10 Hz) or may be 1 sec interval so that visual observation can be conducted. Moreover, the display of the compound distribution and the switching display of the time series images may be selected for the display of the distribution image.

In a case where the distribution image is updated and displayed at the certain time interval, the data indicating the time fluctuation of the characteristic information is also preferably updated and displayed. A color, a size, and the like of plot points corresponding to the distribution images displayed in parallel are preferably changed in accordance with the update of the distribution image. In a case where the obtained distribution image and the data indicating the time fluctuation are all updated and displayed, the display may be returned to the redisplay or the display of the first obtainment.

Furthermore, the distribution image and the data indicating the time fluctuation may indicate mutually different characteristic information. To elaborate, the distribution of the absorption coefficient (the first characteristic information) is indicated as the distribution image, and the data indicating the time fluctuation of the oxygen saturation (the second characteristic information) may be displayed as the data indicating the time fluctuation.

In the above-described example, in a case where the input of the parallel display mode from the user is received, the data indicating the time fluctuation of the characteristic information 240 and the distribution image 202 are displayed in parallel (that is, if the input of the parallel display mode does not exist, only the distribution image 202 is displayed). However, in a case where the distribution image is displayed, the data indicating the time fluctuation of the characteristic information in a predetermined region may be displayed automatically (by default). Furthermore, the processing apparatus 140 may selectively execute the parallel display mode and the sole display mode. To elaborate, in a case where the sole display mode is input by the user, the distribution image and the data indicating the time fluctuation of the characteristic information are not displayed in parallel, and only one of the distribution image and the data indicating the time fluctuation of the characteristic information may be displayed.

According to the present embodiment, even in a case where the measurement such as the light irradiation and the reception of the acoustic wave continues, and the distribution image is updated, once the ROI is set, the time fluctuation of the characteristic information in the set ROI is also preferably updated in accordance with the update of the distribution image.

Hereinafter, applied examples according to the present embodiment will be described. Specifically, the calculation for the characteristic information in the specified ROI and the plotting of the value of the characteristic information are repeated by repeating S104 and S105. As a result, the data 240 in which the value of the characteristic information is updated.

Applied Example 1

According to the present applied example, only a part of the characteristic information in the ROI is used instead of using all the characteristic information in the ROI in a case where the processing apparatus 140 obtains the statistic amount of the plural characteristic information in the ROI. Specifically, a threshold is set for the value (signal intensity) of the characteristic information, and only the characteristic information that satisfies the threshold is used to calculate the average value or the like. Typically, the characteristic information having the value (signal intensity) of the characteristic information equivalent to an intensity at the level of noise is excluded, and the characteristic information having a value higher than the predetermined threshold may be used. In a case where 80 dB at the level of noise is set as the threshold, the characteristic information having the signal intensity lower than or equal to 80 dB is excluded, and the characteristic information having the signal intensity higher than 80 dB may be used for obtaining the average.

An upper limit threshold (for example, 150 dB) may also be prepared instead of the lower limit threshold. The characteristic information where the signal intensity is spontaneously increased is excluded, and the characteristic information having the signal intensity lower than 150 dB may be used for obtaining the average. Furthermore, both the lower limit threshold and the upper limit threshold may be prepared.

In this manner, it is possible to exclude the characteristic information having the noise or the spontaneous fluctuation value by preparing the lower limit threshold, the upper limit threshold, or the combination of those in a case where the statistic amount is obtained even when the statistic amount is other than the average. Therefore, the time fluctuation of the characteristic information in the more effective region can be extracted, and it is more facilitated to check the time fluctuation of the characteristic information.

Applied Example 2

According to the present applied example, a feature resides in that the processing apparatus 140 sets plural ROIs in response to an input from the user. FIG. 6 is a schematic diagram of a display screen according to the present applied example. First, the user confirms an ROI setting icon 330 by a mouse cursor displayed on the screen, a rectangular ROI 320 is displayed on the distribution image 302. When the user moves the ROI 320 to a desired position and confirms the movement, the processing apparatus 140 displays data 340 indicating the time fluctuation of the statistic amount of the characteristic information in the ROI 320 in response to the setting of the ROI 320.

Furthermore, when the user clicks the ROI setting icon 330 again, another rectangular ROI 321 is displayed on the distribution image 302. When the user moves the ROI 321 to a desired position and confirms the movement, the processing apparatus 140 displays data 341 indicating the time fluctuation of the statistic amount of the characteristic information in the ROI 321.

In this manner, since the plural ROIs can be set, it is possible to observe the changes in the characteristic information of the ROIs at the plural positions in the same distribution image at the same time. Therefore, since a magnitude of the signal of the characteristic information or a difference in an amplification amount between different regions can easily be recognized, for example, it is possible to check a difference in a conveyance state of blood or medicine or the like, and the diagnosis accuracy may further be improved.

Second Embodiment

The present embodiment is different from the first embodiment in the processing content by the processing apparatus 140. The subject information obtaining apparatus according to the present embodiment uses an apparatus having a configuration similar to the apparatus illustrated in FIGS. 1A and 1B and FIGS. 3A and 3B. In addition, since an outline of the display method is also basically the same as the flow described in FIG. 4, a part different from the first embodiment will mainly be described below by using FIG. 7.

A feature of the present embodiment resides in that the compound distribution is created again on the basis of the data indicating the time fluctuation of the characteristic information. FIG. 7 is a schematic diagram for describing the data indicating the time fluctuation of the characteristic information 401 displayed according to the present embodiment.

The data indicating the time fluctuation of the characteristic information illustrated in FIG. 7 is data created by the method described according to the first embodiment. Specifically, as described in the flow of FIG. 4, the processing apparatus 140 compounds the plural characteristic distributions obtained by the plural light irradiations with each other to display the compound distribution. When the ROI is set in the compound distribution, the processing apparatus 140 calculates the statistic amount of the characteristic information in the ROI for each characteristic distribution used for the compound distribution to be displayed as the time fluctuation of the characteristic information. To elaborate, since the characteristic information for the characteristic distributions obtained by the plural light irradiations are arranged, the data of FIG. 7 is indicated as the time fluctuation of the characteristic information for each light irradiation.

Here, in the data indicating the time fluctuation of the characteristic information 401, a specific point 410 where a value is spontaneously increased and a specific point 411 where a value is spontaneously decreased are checked. It is conceivable that the specific point 410 and the specific point 411 are generated from an influence of a relative displacement between the probe and the subject at the time of the measurement or the like. However, since the displayed compound distribution is compounded by also using the characteristic distribution in the time corresponding to the specific point 410 or the specific point 411, a reliability may be decreased.

In view of the above, according to the present embodiment, while the user specifies the specific point 410 or the specific point 411 by using the mouse, the processing apparatus 140 can create the compound distribution again by excluding the characteristic distribution in the time specified the specified specific point 410 or the specified specific point 411. Therefore, according to the present embodiment, it is possible to present the distribution image having an even higher reliability.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

In addition, embodiments are also realized by executing the following processing. That is, the processing is executed while software (program) that realizes the above-described respective embodiments is supplied to a system or an apparatus via a network or various storage media, a computer (or a CPU, an MPU, or the like) of the system or the apparatus reads out and executes the program.

According to the embodiments of the present invention, it is possible to perform the presentation useful to the diagnosis with the satisfactory usability for the user.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-286683, filed Dec. 28, 2012 and No. 2013-240119, filed Nov. 20, 2013, which are hereby incorporated by reference herein in their entirety.

REFERENCE SIGNS LIST

110 Light source
120 Outgoing terminal
130 Probe
131 Transducer element
140 Processing apparatus
160 Display apparatus

The invention claimed is:

1. A subject information obtaining apparatus comprising:
a processing unit configured to obtain a plurality of pieces of characteristic information based on acoustic waves generated by light irradiation of a subject with light a plurality of times,
wherein the processing unit is further configured to:
obtain first characteristic information and second characteristic information of a kind different from that of the first characteristic information as the characteristic information, and causes a display unit to display, within same screen, a distribution image generated by using a characteristic distribution of the first characteristic information and data indicating a time fluctuation of the second characteristic information in a region, and the region is-determined based on an instruction of a user for the distribution image;
generates a compound distribution by compounding the plurality of characteristic distributions of the first characteristic information corresponding to the plurality of times, as the distribution image; and
generates the data indicating the time fluctuation of the second characteristic information corresponding to the plurality of times;
wherein the processing unit can selectively execute at least a parallel display mode and a sole display mode, and the processing unit causes the display unit to display the distribution image corresponding to the compound distribution based on the first characteristic information and the data indicating the time fluctuation of the second characteristic information in a case where an input of the parallel display mode by a user is received and not to display the distribution image and the data indicating the time fluctuation of the second characteristic information in a case where the input of the parallel display mode does not exist or a case where the input of the sole display mode from the user is received.

2. The subject information obtaining apparatus according to claim 1,
wherein the processing unit calculates a statistic amount of the characteristic information in the region, and causes the display unit to display data indicating a time fluctuation of the statistic amount as the data indicating the time fluctuation of the characteristic information.

3. The subject information obtaining apparatus according to claim 1,
wherein the processing unit obtains first characteristic information and second characteristic information different from the first characteristic information as the characteristic information and causes the display unit to display image information including the distribution image generated by using a characteristic distribution indicating a distribution of a plurality of pieces of the first characteristic information each of which corresponding to a different one of a plurality of positions in the subject and the data indicating the time fluctuation of the second characteristic information in the region of the distribution image.

4. The subject information obtaining apparatus according to claim 1, wherein the processing unit obtains information on which at least one of a sound pressure of the acoustic waves generated when the light is absorbed, an absorption coefficient of the light, an oxygen saturation, and a material concentration is reflected as the characteristic information.

5. The subject information obtaining apparatus according to claim 1, further comprising:
a plurality of transducer elements configured to receive the acoustic waves generated through the light irradiation and transduce the acoustic waves into a plurality of first reception signals; and
a plurality of transducer elements configured to transmit the acoustic waves, receive reflection waves reflected in the subject, and transduce the reflection waves into a plurality of second reception signals,
wherein the processing unit generates the characteristic distribution, a distribution related to an acoustic characteristic by using the plurality of second reception signals, and generates a superposition image obtained by superposing the characteristic distribution and the distribution related to the acoustic characteristic on each other as the distribution image.

6. The subject information obtaining apparatus according to claim 5, wherein the plurality of transducer elements configured to receive the acoustic waves generated through the light irradiation and the plurality of transducer elements configured to transmit the acoustic waves and receive the reflection waves are common to each other.

7. A display method of displaying an image on a display unit by using a plurality of pieces of characteristic distribution based on acoustic waves generated by light irradiation of a subject with light irradiation of a subject a plurality of times, the display method comprising:
obtaining first characteristic information and second characteristic information of a kind different from that of the first characteristic information as the characteristic information, and
displaying display information, within same screen, including a distribution image generated by using the characteristic distribution of the first characteristic information and data indicating a time fluctuation of the second characteristic information in a region, the region determined based on an instruction of a user for the distribution image, wherein the displaying includes:
generating a compound distribution by compounding the plurality of characteristic distributions of the first characteristic information corresponding to the plurality of times as the distribution image, and
generating the data indicating the time fluctuation of the second characteristic information corresponding to the plurality of times,
wherein the processing unit can selectively execute at least a parallel display mode and a sole display mode, and the processing unit causes the display unit to display the distribution image corresponding to the compound distribution based on the first characteristic information and the data indicating the time fluctuation of the second characteristic information in a case where an input of the parallel display mode by a user is received and not to display the distribution image and the data indicating the time fluctuation of the second characteristic information in a case where the input of the parallel display mode does not exist or a case where the input of the sole display mode from the user is received.

8. The display method according to claim 7, wherein the displaying includes displaying data indicating a time fluctuation of a statistic amount of the characteristic information in the predetermined region as the data indicating the time fluctuation of the characteristic information.

9. The display method according to claim 7, wherein the obtained characteristic information includes first characteristic information and second characteristic information different from the first characteristic information, and wherein the displaying includes displaying the distribution image generated by using a characteristic distribution indicating a distribution of a plurality of pieces of the first characteristic information each of which corresponding to a different one of a plurality of positions in the subject and the data indicating the time fluctuation of the second characteristic information in the region of the distribution image.

10. The display method according to claim 7, further comprising:
obtaining information on a distribution related to an acoustic characteristic in the subject generated by transmitting acoustic waves and receiving reflection waves reflected in the subject, wherein the displaying includes displaying a superposition image obtained by superposing the characteristic distribution and the distribution related to the acoustic characteristic on each other as the distribution image.

11. A non-transitory computer-readable storage medium which records a program for causing a computer to execute the respective steps of the display method according to claim 7.

12. The subject information obtaining apparatus according to claim 1, further comprising:
a light source that generates light;
a plurality of transducer elements configured to receive acoustic waves generated in a subject that is irradiated with the light from the light source and transduce the acoustic waves into a plurality of reception signals.

13. The subject information obtaining apparatus according to claim 1, wherein the data indicating the time fluctuation of the characteristic information is a line chart.

14. The display method according to claim 7, wherein the data indicating the time fluctuation of the characteristic information is a line chart.

15. The subject information obtaining apparatus according to claim 1, wherein image reconstruction is a reverse projection method based on a time domain or a Fourier domain.

16. The display method according to claim 7, wherein image reconstruction is a reverse projection method based on a time domain or a Fourier domain.

17. The subject information obtaining apparatus according to claim 1, wherein the characteristic distribution indicates a 2D or 3D distribution of the plurality of pieces of characteristic information, each of which corresponding to a different one of the plurality of positions in the subject.

18. The display method according to claim 7, wherein the characteristic distribution indicates a 2D or 3D distribution of the plurality of pieces of characteristic information, each of which corresponding to a different one of the plurality of positions in the subject.

19. The subject information obtaining apparatus according to claim 1, wherein the processing unit causes the display unit to display the image information and data indicating a time fluctuation of the characteristic information in each of a plurality of regions of the distribution image, and each of the plurality of regions is a region determined based on an instruction of the user for the distribution image.

20. The display method according to claim 7, wherein displaying includes data indicating a time fluctuation of the characteristic information in each of a plurality of regions of the distribution image, the plurality of regions being a region determined based on an instruction of the user for the distribution image.

21. The subject information obtaining apparatus according to claim 3, wherein the processing unit obtains an absorption coefficient as the first characteristic information and an oxygen saturation as the second characteristic information.

22. The display method according to claim 9, wherein the first characteristic information is an absorption coefficient and the second characteristic information is an oxygen saturation.

* * * * *